(12) United States Patent
Borkan

(10) Patent No.: US 6,662,053 B2
(45) Date of Patent: Dec. 9, 2003

(54) MULTICHANNEL STIMULATOR ELECTRONICS AND METHODS

(76) Inventor: William N. Borkan, 3142 NE. 166$^{th}$ St., North Miami Beach, FL (US) 33160

( * ) Notice: Subject to any disclaimer, the term of this patent is extended or adjusted under 35 U.S.C. 154(b) by 292 days.

(21) Appl. No.: 09/837,652

(22) Filed: Apr. 19, 2001

(65) Prior Publication Data

US 2002/0022866 A1 Feb. 21, 2002

Related U.S. Application Data

(60) Provisional application No. 60/225,731, filed on Aug. 17, 2000.

(51) Int. Cl.$^7$ ............................. A61N 1/18; A61N 1/32
(52) U.S. Cl. .................... 607/59; 607/14; 607/44; 607/66; 607/70
(58) Field of Search .................... 607/48, 59, 66, 607/70, 72, 14, 16, 42, 40, 44

(56) References Cited

U.S. PATENT DOCUMENTS

| | | | |
|---|---|---|---|
| 3,449,768 A | 6/1969 | Doyle | |
| 3,727,616 A | 4/1973 | Lenzkes | 128/422 |
| 4,379,462 A | 4/1983 | Borkan et al. | 128/786 |
| 4,459,989 A | * 7/1984 | Borkan | 607/60 |
| 4,612,934 A | * 9/1986 | Borkan | 607/62 |
| 4,793,353 A | * 12/1988 | Borkan | 607/60 |
| 4,935,345 A | 6/1990 | Guilbeau et al. | 435/14 |
| 5,649,970 A | 7/1997 | Loeb et al. | 607/57 |
| 5,895,416 A | 4/1999 | Barreras, Sr. et al. | 607/62 |
| 5,913,882 A | 6/1999 | King | 607/62 |
| 5,938,690 A | 8/1999 | Law et al. | 607/46 |
| 5,941,906 A | 8/1999 | Barreras, Sr. et al. | 607/66 |
| 6,052,624 A | 4/2000 | Mann | 607/46 |

* cited by examiner

Primary Examiner—Hieu T. Vo
Assistant Examiner—Johnny H. Hoang
(74) Attorney, Agent, or Firm—Barnes & Thornburg

(57) ABSTRACT

A tissue stimulation system includes an electrode assembly having at least three electrodes spaced to be stimulated in a patient. A programmable stimulator is connected to and provides stimulation pulses to the electrode assembly. A programming data in the stimulator defines, for each of the at least three electrodes, individual stimulation pulses of varying polarity and at least one of amplitude, frequency, pulse width and pulse shape.

35 Claims, 3 Drawing Sheets

MULTICHANNEL STIMULATOR ELECTRONICS AND METHODS

CROSS-REFERENCE

This application claims priority of Provisional Application Ser. No. 60/225,731 filed Aug. 17, 2000.

BACKGROUND AND SUMMARY OF THE INVENTION

The present invention relates to a tissue stimulator system and methods of use.

The concept of using electronic stimulation systems for the purpose of controlling nerves or muscles is well known. These systems typically utilize an implantable or an external pulse generator. The external systems consist of a transmitter and antenna which transmits energy and/or stimulation signals transcutaneously through a patient's skin to an implanted receiver. The receiver provides signal processing of the received pulses and transmits the energy derived therefrom to activate electrodes implanted adjacent to specific types of tissue to be stimulated. A system like the one described above has been disclosed previously in U.S. Pat. No. 3,727,616. It is also known in prior art where more than one pair of electrodes are activated such as U.S. Pat. No. 3,449,768.

Problems arise in these prior art systems where electrode placement fails to provide the desired physical response. It may also occur later if a change in patient condition or change in electrode position occurs. This failure may also be caused by improper polarity of the stimulated electrodes relative to one another. Furthermore, it is often required that the electrodes be implanted surgically adjacent to one or more nerve fibers. This type of procedure involves inherent risks due to the fact that it is often performed in close proximity to the brain or spinal cord or other sensitive nerves or tissues. It is therefore desirable to perform the electrode implantation only once to minimize the surgical risks to the patient as well as the financial burdens.

Moreover, even when a plurality of electrodes have been utilized, such that repeated surgical procedures are not required, the prior art systems did not provide for dynamic programming and reprogramming of different electrodes after surgery until U.S. Pat. No. 4,459,989 to Borkan. The Borkan patent '989 disclosed an external stimulator system which allowed noninvasive programming of the stimulated electrodes. Each electrode was capable of assuming a positive, negative or open circuit status with respect to the other electrodes. This effectively allowed the electrodes to be "repositioned" non-invasively. That same programming ability (plus/minus/off) was later applied to totally implantable systems as well. The system had mono/biphasic control also.

Further improvements are described in U.S. Pat. No. 4,612,934 also to Borkan. The Borkan patent '934 provides programming to the surgically implanted stimulator receiver to define electrode selection and polarity and stimulation pulse parameters. The pulse parameters included frequency, amplitude and pulse width. The impedance of the electrodes are measured and used to modify the programmed stimulation pulse as were inputs from measured physical parameters. A single stimulation pulse was developed and provided to any or all the selected electrode combinations. There was not the ability to provide individual pulses simultaneously to different selected electrodes. Also, the impedance of the individual electrodes were not measured, but only the electrodes as a group.

A tissue stimulation system includes an electrode assembly having at least three electrodes spaced to be stimulated in a patient. A programmable stimulator is connected to and provides stimulation pulses to the electrode assembly. A programming data in the stimulator defines, for each of the at least three electrodes, individual stimulation pulses of varying polarity and at least one of amplitude, frequency, pulse width and pulse shape.

The stimulator may include a pulse generator for each of the electrodes, or a common pulse generator for all the electrodes and a variable impedance circuitry for each of the electrodes. A variable impedance circuit may include a voltage divider or an analog switch, for example. The stimulator would individually control the amplitude and pulse width using the variable impedance circuit.

The stimulator can measure the impedance of each of the electrodes and modifies the stimulation pulse for each electrode defined by the programming data as a function of the measured impedance of that electrode.

Also, the stimulator may measure physical or physiological parameters and modifies the stimulation pulse for each electrode defined by the parameter data as a function of the measured parameters. The measured parameters may include one of the following: EMG, EKG, or EEG measurements. The measurement circuit may include chemical or biochemical sensors. The stimulator includes a signal input and modifies the stimulation pulses as a function of input signals on the signal input. The input signals may include processed audio or visual signals.

The stimulator may determine the position of the electrode from the measured parameters and modifies the stimulation pulses as a function of the determined position. A display is provided for showing the determined position.

An additional electrode spaced from the at least three electrodes is provided. The additional electrode has a surface area greater than the surface area of each of the at least three electrodes. The additional electrode is at least twice the surface area of each of the at least three electrodes. The additional electrode is spaced from the at least three electrode by at least 10 millimeters.

The programming data defines bipolar mode, monopolar mode and simultaneous bipolar/monopolar mode stimulation. The bipolar mode uses at least two of the at least three electrodes and the monopolar mode uses the additional electrode as an anode electrode and at least one of the at least three electrodes as a cathode electrode.

The present tissue stimulation system maybe used to perform a method of tissue stimulation by positioning the electrode assembly with the electrodes lying along a tissue to be stimulated in the patient and the stimulator connected to the electrodes. Stimulation pulses are provided from the stimulator to the at least three electrodes with independently assigned polarity and at least one of amplitude, frequency, pulse width and pulse shape. The stimulator may be external or preferably implanted.

The method may further include measuring the series impedance of each of the electrodes and modifying the stimulation pulse for each electrode defined as a function of the measured impedance of that electrode.

Additionally, physical or physiological parameters can be measured and the simulation pulse modified for each electrode defined as a function of the measured parameters. The measured parameters may include one of the following: EMG, EKG, or EEG measurements. Information may be obtained from at least one of pulmonary, cardiac or neuro monitors; and the stimulation pulses are modified as a function of the information and measured parameters.

Additionally, the relative position of the electrodes to the desired tissue to be stimulated may be determined using the measured parameters. The determined electrode's relative position may be displayed. The display may show overlays of an image of the desired electrode position and/or movement on an x-ray or fluoroscopic image. The system provides feedback to a physician as the electrode is moved in real time.

The stimulation pulses may be modified as a function of the relative position. The measuring may include EMG measurements of specific muscles. The stimulation pulses are modified to determine the relative position of one or more of the individual electrodes.

The method may also include simultaneously providing stimulation pulses to at least two of the at least three electrodes in a bipolar mode and to an additional electrode as an anode and at least one of the at least three electrodes as a cathode in a monopolar mode.

Other objects, advantages and novel features of the present invention will become apparent from the following detailed description of the invention when considered in conjunction with the accompanying drawings.

DETAILED DESCRIPTION OF THE PREFERRED EMBODIMENTS

Figure 1:
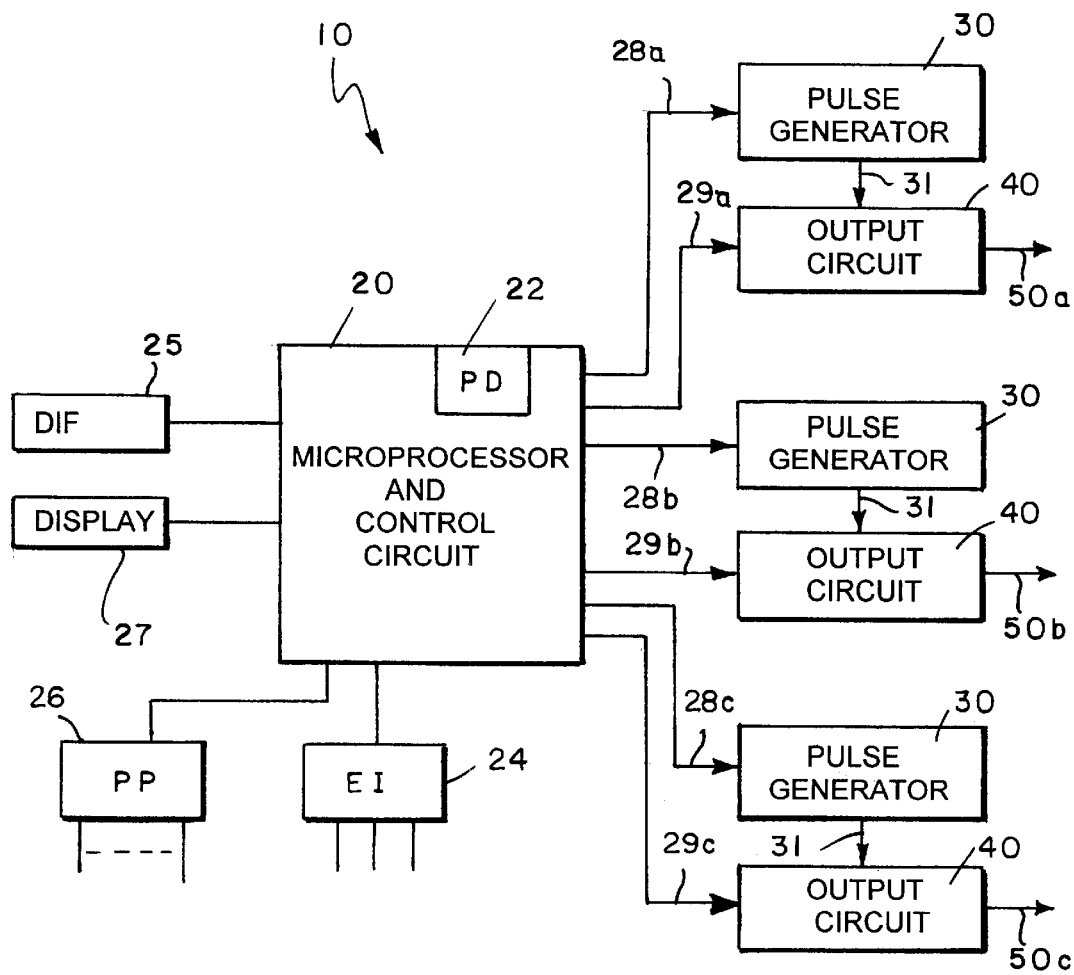
FIG. 1 is a block diagram of a stimulator system according to the principles of the present invention.

Current neurostimulation leads are placed in or near the spinal cord, brain or individual nerves and the power required to generate functional stimulation is determined directly by the size, shape, material, configuration and orientation of the active electrode contacts. Decreasing the surface area of the electrode results in decreased power requirements from the stimulator in order to create the same functional effect due to increased field density.

Electrodes used for spinal cord stimulation are typically implanted in the epidural space. This is done for various reasons, including reduced complexity of the surgery, reduced potential complications, an increased stability of the implant. However, implantation in the epidural space requires a significant amount of additional stimulation power since the signal must be transmitted through the dura and cerebrospinal fluid in order to reach its desired neural targets in the spinal cord.

Limitations of the currently available systems to refine the delivered stimulation field often lead to ineffective therapy and/or additional surgical intervention. Current state of the art systems use reprogramming of relative electrode polarity to effectively "move" the stimulation field non-invasively. The object of the present invention is to provide additional and more sensitive methods to move the stimulation field (and therefore the activated neural fibers and tissues) to achieve effective therapy.

The present invention alters the size, shape, and position of the electrical field by changing the relative amplitude or impedance of the stimulation pulse for the stimulated electrodes individually. For instance, if four electrodes are activated-two as cathodes and two as anodes—the electrical field may be altered by changing the relative amplitude, pulse width and/or pulse shape delivered to the individual electrodes.

Many applications of electrical stimulation in nervous tissue (including the brain, spinal cord, auditory and visual nerve fibers) require very precise positioning of the electrical field to achieve the desired effects. Further advances in the treatment of spinal cord injury and treatment of paralyzed limbs will also require highly refined methods of activating targeted tissues and nerve fibers.

The present invention provides the highly refined targeting capabilities for optimal therapeutic results. Use of independent amplitude control allows reprogramming of an electrode array to compensate for less than optimal position relative to the targeted neural fibers. For instance, two catheters placed off the midline of the spinal cord may stimulate undesirable nerve roots at the levels required to activate desired longitudinal fibers making it impossible to achieve acceptable therapeutic results with a conventional stimulator. By changing the relative amplitude of the stimulation pulse for the electrodes individually the stimulation field can be moved to avoid activating the undesirable fibers.

Some nerve fibers are more sensitive to different pulse shapes or pulse widths. Altering these parameters for each electrode individually allows more selective activation of desired neural targets while minimizing activation of undesirable structures.

The method could further include measuring certain physical or physiological parameters and modifying the stimulation pulses based on these measurements. For instance, during implantation of a spinal cord stimulator, placement of the electrode at a specific dermatomal location and/or lateral position relative to the spinal cord is critical. Measurement of stimulation induced muscle contractions by a series of individually generated stimulation pulses can be performed such that a system to indicate when the desired location is achieved based on physiological measurements becomes practical. Without individual pulse parameter control, this procedure would be time consuming, impractical and in many instances impossible.

A stimulator 10 is shown in FIG. 1 as including a microprocessor and control circuit 20 having programming data 22 stored therein. The programming data determines which electrodes are to be stimulated, the polarity of the electrodes relative to each other, and the stimulator pulse to be applied to each of the individual electrodes defined. Although the programming data is shown stored in the circuit, it could be stored externally or downloaded from an external source via interface 25. The data may be downloaded on a pulse to pulse basis, for instance in an auditory or visual prosthetic application.

The microprocessor control circuit 20 may also include measurement circuits to measure the impedance of each electrode through electrode impedance measuring element 24 which senses the impedance of each of the individual electrode. It may also monitor physical or physiological parameters using measurement circuit 26. The measurement circuit 26 may include chemical or biochemical sensors. These physical parameters may be biological parameters or other information. The measured parameters may include one of the following: EMG, EKG, or EEG measurements received via interface 25. Information may be obtained via interface 25 from at least one of pulmonary, cardiac or neuro monitors.

Additionally, the relative position of the electrodes to the desired tissue to be stimulated may be determined using the measured parameters. The stimulation pulses may be modified as a function of the relative position. The measuring may include EMG measurements of specific muscles. The stimulation pulses are modified to determine the relative position of one or more of the individual electrodes. The determined electrode's relative position may be displayed. The display 27 may show overlays an image of the desired electrode position and/or movement on an x-ray or fluoroscopic image. The system provides feedback to a physician as the electrode is moved in real time.

The microprocessor and control circuit 20 may modify the programming data 22 based on one or all of these measured parameters as well as the determined position. This will vary which electrodes are to be stimulated, their polarity relative to each other and the stimulation pulse for each of the individual electrodes. The measured parameters may be stored and/or transmitted via the interface 25.

Control information is provided from the microprocessor and control circuit 20 to a pulse generator 30 via line 28 and to an output circuit 40 via line 29 for each electrode. The pulse generator 30 provides a stimulation pulse to the output circuit 40 via line 31. The output 50 of the output circuits 40 are connected to individual electrodes. There is a pulse generator circuit 30 and an output circuitry 40 for each of the individual electrodes. Three are shown for sake of clarity. This system allows each of the individual electrodes to have its individually defined pulse generator.

Figure 2:
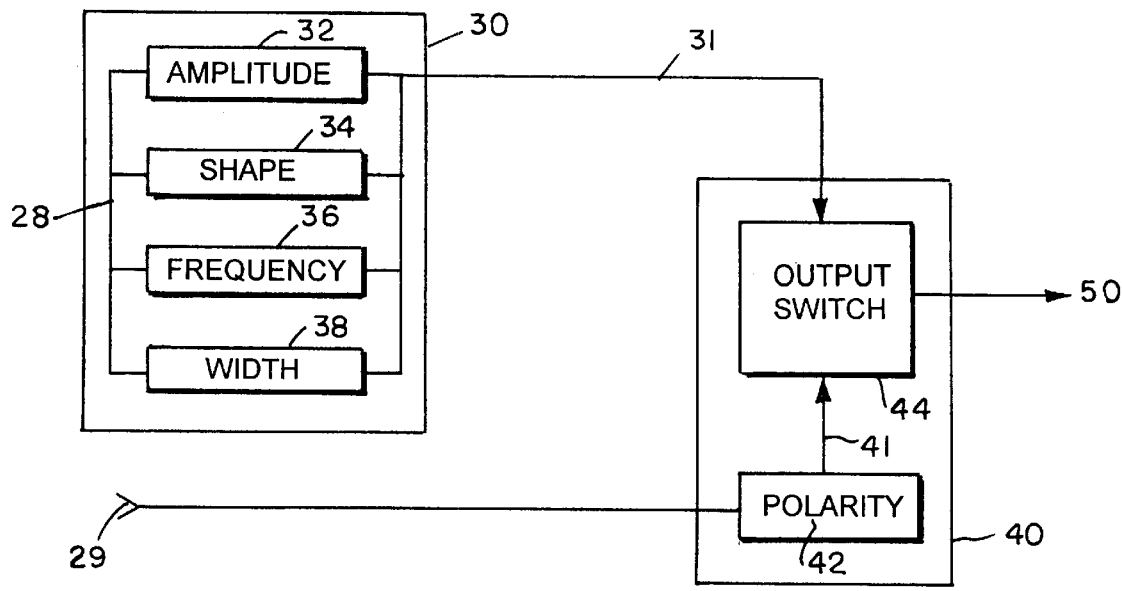
FIG. 2 is a block diagram of a first embodiment of portions of stimulator system using individual pulse generators for each electrode according to the principles of the present invention.

FIG. 2 shows further details of the pulse generator circuit 30 and the output circuitry 40. The pulse generator 30 includes also an amplitude defining circuit 32, pulse shape defining circuit 34, frequency defining circuit 36 and a pulse width defining circuit 38. Control of each of these are from the stimulation microprocessor control circuitry 20 via line 28.

The output circuit 40 also includes an electrode polarity circuit 42 receiving controls from the microprocessor control circuitry 25 via line 29. The output of the electrode polarity circuit 42 is provided via line 41 to the output switch 44. The pulse on line 31 from the pulse generator 30 may be transmitted by the output switch 44 to the electrode at output 50, depending upon the polarity or high impedance as determined by electrode polarity circuit 42. The electrode may either be in a positive, negative or high impedance state.

Figure 3:
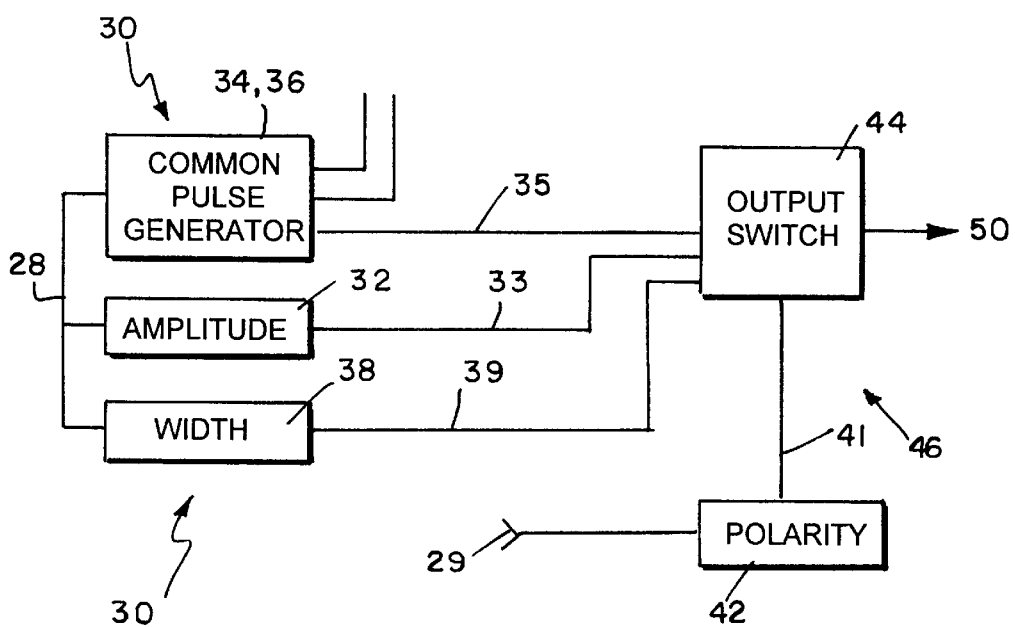
FIG. 3 is a block diagram of a portion of the stimulator including a common pulse generator with individual pulse width and amplitude modification for each electrode according to the principles of the present invention.

A modification is illustrated in FIG. 3. A common pulse generator 34, 36 provides at output 35 to the output switch 44 a pulse of a shape and frequency defined by the control on line 28 from the microprocessor and control circuitry 20. The pulse amplitude circuit 32 also provides an output on line 33 to the output switch 44 as does pulse width circuit 38 via output on line 39.

The pulse amplitude circuit 32 and pulse width circuit 38 modify the common pulse received on line 35 by controlling the output switch 44. The amplitude input via line 33 could control a variable impedance network, which may be a resister divider array controlled by a multiplexer. The pulse width input via line 39 controls the on/off of the switch to determine the pulse width. This could also generate a timing change in the delivered pulses (starting later and ending sooner than other outputs). The polarity is still determined by electrode polarity circuit 42.

Figure 4:
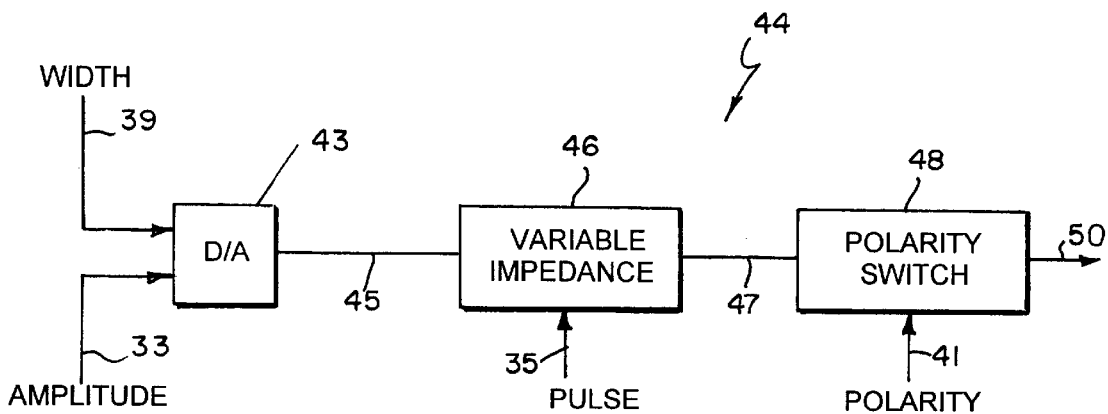
FIG. 4 is a block diagram of an output circuit according to the principles of the present invention.

A more detailed explanation of the output switch 44 is illustrated in FIG. 4. A digital to analog converter 43 receives a pulse amplitude signal over line 33 and the pulse width signal over line 39. This is converted to an analog signal on line 45. The analog signal on line 45, is provided to a variable impedance circuit 46, which also receives the common pulse on line 35, and controls the variable impedance 46 to modify the common pulse. The individual designed pulse is then provided via line 47 to a polarity switch 48 which receives the polarity control on line 41. The output is provided on output 50 to the individual electrode. Alternatively, the pulse width control on line 39 may be used with logic to control the polarity switch 48.

The variable impedance network may be a switch, for example an FET operated in the analog region. The analog switch impedance can vary from ON, being less than 10 ohms, to an off, being greater than one megohms. The variable impedance would typically operate in the range of a few hundred to a few thousand ohms range. This will produce a voltage divider effect since the nerve tissue being stimulated has a nominal impedance of 500–1200 ohms.

The measurement circuits 24,26 could be implemented to interact with the implanted microprocessor 20 to automatically reprogram the stimulation parameters. This would dynamically reprogram a stimulation regimen in response to measured parameters to a programmed level. The methods described herein may also be performed wherein the stimulator 10 is external the patient.

Figure 5:
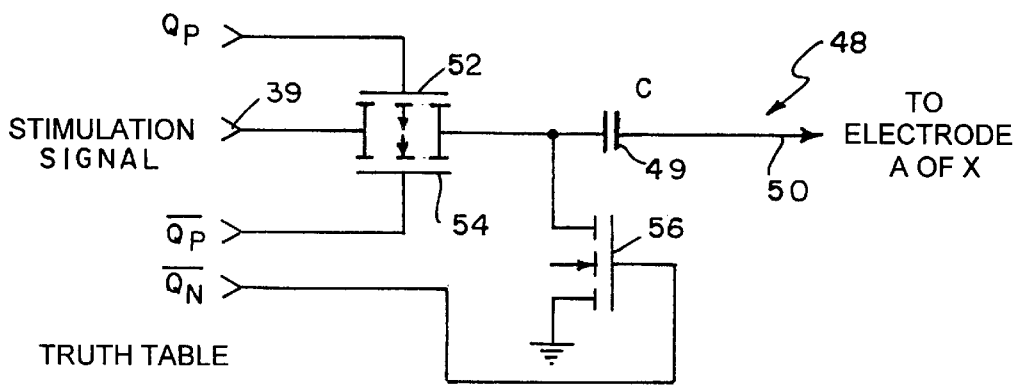
FIG. 5 is a schematic of an embodiment of a polarity switch according to the principles of the present invention.

The polarity switch is illustrated in FIG. 5 as including a pair of complementary field effect transistors 52 and 54 connected in parallel and receiving an analog stimulation pulse 39 to be transmitted depending upon the inputs Qp and Qp(bar) at the respective gates. The output is connected through capacitor 49 to the electrode output 50. A third FET 56 is connected between the capacitor 49 and ground and controlled at its gate by input Qn(bar). If Qn is high, the output polarity is positive. If QP is high, the output is negative. If Qn and Qp are both high, the output is open or high impedance.

For more detailed explanation of the circuitry, reference should be made to U.S. Pat. Nos. 4,459,989 and 4,612,934 both to Borkan, incorporated herein by reference.

Although the present stimulator system has been designed to allow the capability of providing individually designed stimulation pulses for each of the electrodes, the system could operate as a conventional neurostimulator system using delivery of a common stimulation pulse to select electrodes.

Figure 6:
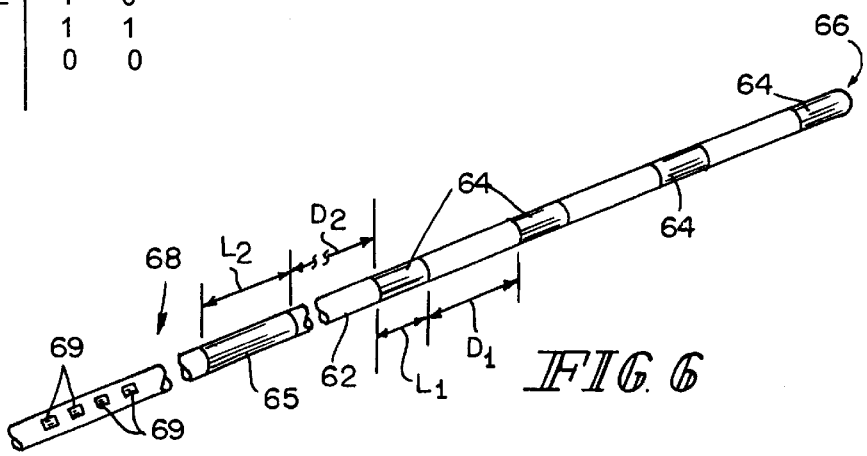
FIG. 6 is a perspective view of a lead with an additional electrode according to the principles of the present invention.

As illustrated in FIG. 6, an electrode 60 includes a sheath 62 having a plurality of in-line electrodes 64 and an additional electrode 65 on a sheath wire extension 67 extending from the distal end 66. The proximal end 68 has contacts 69 connected to each electrode and to the stimulator outputs 50. The additional electrode 65 has a greater surface area on the sheath/wire than the surface area on the sheath of each of the electrodes 64.

The electrodes 64 all may have a length L1 and the additional electrode 65 has a length L2. Length L2 is greater than L1, at least twice its length. Thus, for example, if length L1 is two millimeters, the length L2 is four millimeters. The length L2 may be anywhere between 2–4 times that of the length L1. Also, the additional electrode 66 may have a greater circumferential dimension than each of the electrodes 64. The additional electrode 65 may have a 360° circumference and the electrodes 64 be 180° or less, for example.

Also, it should be noted that the additional electrode 65 is spaced by a distance D2 from the nearest electrode 64. Where D1 is approximately six millimeters, the distance D2 is at least 10 millimeters and can be as much as 20 millimeters or more. With this distance, the electrode acts as a point source when used in conjunction with a second electrode. The electrodes 64 each acts as a point source when used in conjunction with the additional electrode 65 of the increased area.

Although a specific electrode is illustrated in FIG. 6, other electrodes may be used with the stimulator system of the present invention. This is an example of an electrode which is capable of simultaneous operation in a bipolar mode and a monopolar mode as well as each mode alone. In the bipolar mode, at least two of the contacts 64 are used while in the monopolar mode, the additional electrode 65 is used as an anode with at least one of the electrodes 64 as a cathode. The individual programming of the stimulation pulse allows this to occur.

These stimulation paradigms could include sophisticated programs that switch stimulation between a number of electrodes slowly (over seconds or minutes, hours or days) to avoid accommodation of the stimulation or to treat multiple neural targets, or could be fast (approximately the same speed of the electrical activity of neurons in the spinal cord) artificially generating neural signals along the spinal cord or a nerve which could be perceived as any other sensory function with signals that travel through the spinal cord or nerve. For instance, a signal could be generated that would correspond to heat being applied to a patient's big toe, or pressure being applied to a patient's foot, or the sensation of a limb in a different orientation than it actually is.

Theoretically, tastes, smells, sights or even thoughts could be created in this manner allowing various artificial prosthesis (visual, auditory, etc.) to interface with the human body.

Although the present invention has been described and illustrated in detail, it is to be clearly understood that the same is by way of illustration and example only, and is not to be taken by way of limitation. The spirit and scope of the present invention are to be limited only by the terms of the appended claims.

What is claimed:

1. A tissue stimulation system comprising:
   an electrode assembly having at least three electrodes to be stimulated in a patient
   a programmable stimulator connected to and providing non-isolated stimulation voltage pulses to the electrode assembly; and
   programming data in the stimulator defining, for each of at least three electrodes, individual stimulation voltage pulses of varying polarity and at least one of amplitude, frequency, pulse width and pulse shape.

2. A system according to claim 1, wherein the stimulator includes a pulse generator for each electrode.

3. A system according to claim 1, wherein the stimulator includes a common pulse generator and a separate variable impedance circuit for each electrode.

4. A system according to claim 3, wherein the variable impedance circuit includes a voltage divider for each electrode.

5. A system according to claim 3, wherein the variable impedance circuit includes an analog switch for each electrode.

6. A system according to claim 3, wherein the stimulator individually controls the amplitude and pulse width using the variable impedance circuit.

7. A system according to claim 1, wherein the stimulator measures the series impedance of each of the electrodes and modifies the stimulation pulse for each electrode defined by the programming data as a function of the measured impedance of that electrode.

8. A system according to claim 1, wherein the stimulator measures physical parameters and modifies the stimulation pulse for each electrode defined by the programming data as a function of the measured parameters.

9. A system according to claim 1, including an additional electrode spaced from the at least three electrodes and the additional electrode having a surface area greater than the surface area each of the at least three electrodes.

10. A system according to claim 9, wherein the additional electrode is at least twice the surface area of the surface area of each of the at least three electrodes.

11. A system according to claim 9, wherein the additional electrode is spaced from the at least three electrodes by at least ten millimeters.

12. A system according to claim 9, wherein the programming data defines simultaneously stimulation in a bipolar mode using at least two of the at least three electrodes and in a monopolar mode using the additional electrode as an anode electrode and at least one of the at least three electrodes as a cathode electrode.

13. A system according to claim 9, wherein the programming data defines stimulation in a bipolar mode.

14. A system according to claim 9, wherein the programming data defines stimulation in a monopolar mode using additional electrode as a common anode electrode with at least one of the at least three electrodes as a cathode electrode.

15. A system according to claim 1, including a measurement circuit to measure certain physiological parameters; and wherein the stimulator modifies the stimulation pulses as a function of the measured parameters.

16. A system according to claim 15, wherein the measured parameters include one of the following: EMG, EKG, or EEG measurements.

17. A system according to claim 15, wherein the measurement circuit include chemical or biochemical sensors.

18. A system according to claim 15, wherein the stimulator includes a signal input and modifies the stimulation pulses as a function of input signals on the signal input.

19. A system according to claim 18, wherein the input signals include processed audio or visual signals.

20. A system according to claim 15, wherein the stimulator determines the position of the electrode from the measured parameters and modifies the stimulation pulses as a function of the determined position.

21. A system according to claim 20, including a display for showing the determined position.

22. A method of tissue stimulation using an electrode assembly having at least three electrodes and having a programmable stimulator connected to the electrode assembly, the method comprising:
    positioning the at least three electrodes to lie along a tissue to be stimulated in a patient; and
    providing non-isolated stimulation voltage pulses, from the stimulator to at least three electrodes, with independently assigned polarities and at least one of amplitude, frequency, pulse width and pulse shape.

23. A method according to claim 22, including measuring the series impedance of each of the electrodes and modifying the stimulation pulse for each electrode defined as a function of the measured impedance of that electrode.

24. A method according to claim 22, including measuring physical parameters and modifying the stimulation pulse for each electrode defined as a function of the measured parameters.

25. A method according to claim 22, including simultaneously providing stimulation pulses to at least two of the at least three electrodes in a bipolar mode and to an additional electrode on the sheath as an anode and to at least one of the at least three electrodes as a cathode in a monopolar mode.

26. A method according to claim 22, including implanting the stimulator.

27. A method according to claim 22, including measuring certain physiological parameters; and modifying the stimulation pulses as a function of the measured parameters.

28. A method according to claim 27, wherein the measured parameters include one of the following: EMG, EKG, or EEG measurements.

29. A method according to claim 27, including obtaining information from at least one of pulmonary, cardiac or neuro monitors; and modifying the stimulation pulses as a function of the information and measured parameters.

30. A method according to claim 22, including measuring physical parameters; and determining the relative position of the electrodes to the desired tissue to be stimulated using the measured parameters.

31. A method according to claim 30, including displaying determined the electrode's relative position.

32. A method according to claim 31, wherein the displaying overlays an image of the desired electrode position and/or movement on an x-ray or fluoroscopic image.

33. A method according to claim 30, wherein said system provides feedback to a physician as the electrode is moved in real time.

34. A method according to claim 30, including modifying the stimulation pulses as a function of the relative position.

35. A method according to claim 34, wherein measuring includes EMG measurements of specific muscles; and modifying the stimulation pulses to determine the relative position of one or more of the individual electrodes.

* * * * *